(12) United States Patent
Rabben et al.

(10) Patent No.: US 8,657,750 B2
(45) Date of Patent: Feb. 25, 2014

(54) METHOD AND APPARATUS FOR MOTION-COMPENSATED ULTRASOUND IMAGING

(75) Inventors: Stein Inge Rabben, Oslo (NO); Fredrik Orderud, Oslo (NO); Olivier Gerard, Horten (NO)

(73) Assignee: General Electric Company, Schenectady, NY (US)

( * ) Notice: Subject to any disclaimer, the term of this patent is extended or adjusted under 35 U.S.C. 154(b) by 593 days.

(21) Appl. No.: 12/972,862

(22) Filed: Dec. 20, 2010

(65) Prior Publication Data
US 2012/0157845 A1 Jun. 21, 2012

(51) Int. Cl.
*A61B 8/00* (2006.01)
(52) U.S. Cl.
USPC .......................................... 600/443; 382/128
(58) Field of Classification Search
USPC ................... 600/437, 440, 456, 458; 382/128
See application file for complete search history.

(56) References Cited

U.S. PATENT DOCUMENTS

| 7,454,048 B2 | 11/2008 | Schoisswohl et al. | |
|---|---|---|---|
| 2003/0023166 A1* | 1/2003 | Frisa et al. | 600/443 |
| 2003/0123734 A1* | 7/2003 | Li et al. | 382/190 |
| 2010/0195881 A1 | 8/2010 | Orderud et al. | |

\* cited by examiner

*Primary Examiner* — Parikha Mehta

(57) ABSTRACT

An ultrasound imaging system and method include acquiring first ultrasound data, the first ultrasound data comprising data of a first plane through a structure of interest. The ultrasound imaging system and method include tracking the motion of a landmark based on the first ultrasound data. The ultrasound imaging system and method acquiring second ultrasound data, the second ultrasound data including data of a second plane through the structure of interest, the second plane being distinct from the first plane, where the position of the second plane is adjusted to track the motion of the landmark. The ultrasound imaging system and method also includes generating an image based on the second ultrasound data.

22 Claims, 4 Drawing Sheets

METHOD AND APPARATUS FOR MOTION-COMPENSATED ULTRASOUND IMAGING

FIELD OF THE INVENTION

This disclosure relates generally to a method and system for acquiring motion-compensated ultrasound data.

BACKGROUND OF THE INVENTION

Obtaining anatomically correct ultrasound images with high temporal and spatial resolution is often challenging with conventional ultrasound imaging systems. The imaging of an organ that exhibits significant movement, such as the heart, poses a particularly difficult challenge. For example, with a conventional ultrasound imaging system, a two-dimensional image typically affords the best combination of temporal and spatial resolution. However, if the object being imaged exhibits significant out-of-plane motion, the result will be that the two-dimensional image is not anatomically correct. For example, while acquiring ultrasound data of a plane, as in a conventional two-dimensional acquisition, the plane is typically defined in a fixed position with respect to an ultrasound probe. Therefore, as the object being imaged moves, different portions of the anatomy may be captured at different times during the image acquisition. For example, if the structure being imaged exhibits significant motion in a generally vertical plane while the plane of the two-dimensional image is generally horizontal, then the two-dimensional image will includes slices from different heights of the object instead of being focused exclusively on the structure of interest.

One way around the aforementioned problem is to acquire volumetric, or three-dimensional ultrasound data of the object. If the volume of acquisition is large enough to include the structure of interest throughout its full range of motion, it is possible to view the structure of interest at multiple phases. However, one problem with acquiring three-dimensional ultrasound data is that it typically takes significantly more time to acquire three-dimensional ultrasound data compared to two-dimensional ultrasound data. As a result, either one or both of the temporal resolution and the spatial resolution typically suffers when viewing a real-time three-dimensional image. If the three-dimensional ultrasound data acquisition is gated over multiple cardiac cycles, it is possible to increase the spatial resolution and the temporal resolution, but then the user may lose the advantage of real-time feedback.

For at least the reasons discussed hereinabove, there is a need for an ultrasound imaging system and method for obtaining anatomically correct ultrasound data with acceptable temporal and spatial resolution.

BRIEF DESCRIPTION OF THE INVENTION

The above-mentioned shortcomings, disadvantages and problems are addressed herein which will be understood by reading and understanding the following specification.

In an embodiment, a method of ultrasound imaging includes acquiring first ultrasound data, the first ultrasound data including data of a first plane through a structure of interest. The method includes tracking the motion of a landmark based on the first ultrasound data. The method includes acquiring second ultrasound data of a second plane through the structure of interest. The second plane being distinct from the first plane, and wherein the position of the second plane is adjusted to track the motion of the landmark. The method also includes generating an image based on the second ultrasound data.

In another embodiment, a method of ultrasound imaging includes acquiring first ultrasound data, the first ultrasound data including data of a first plane through a structure of interest. The method includes interleaving the acquisition of second ultrasound data with the acquisition of the first ultrasound data, the second ultrasound data comprising data of a second plane through the structure of interest, the second plane being disposed at an angle with respect to the first plane. The method includes tracking the motion of a landmark in the first plane based on the first ultrasound data. The method includes adjusting the position of the second plane in real-time based on the motion of the landmark in the first plane, where the position of the second plane is adjusted to maintain a generally constant orientation with respect to the landmark. The method also includes displaying an image generated from the second ultrasound data.

In another embodiment, an ultrasound imaging system includes a probe configured to acquire ultrasound data, a display device, and a processor in electronic communication with both the probe and the display device. The processor is configured to control the probe to acquire first ultrasound data, the first ultrasound data comprising data of a first plane through a structure of interest. The processor is configured to track the motion of a landmark based on the first ultrasound data. The processor is configured to control the probe to acquire second ultrasound data, the second ultrasound data including data of a second plane through the structure of interest. The second plane being distinct from the first plane. Wherein, the position of the second plane is adjusted to track the motion of the landmark. The processor is configured to generate a dynamic image based on the second ultrasound data and to display the dynamic image on the display device.

Various other features, objects, and advantages of the invention will be made apparent to those skilled in the art from the accompanying drawings and detailed description thereof.

DETAILED DESCRIPTION OF THE INVENTION

Figure 1:
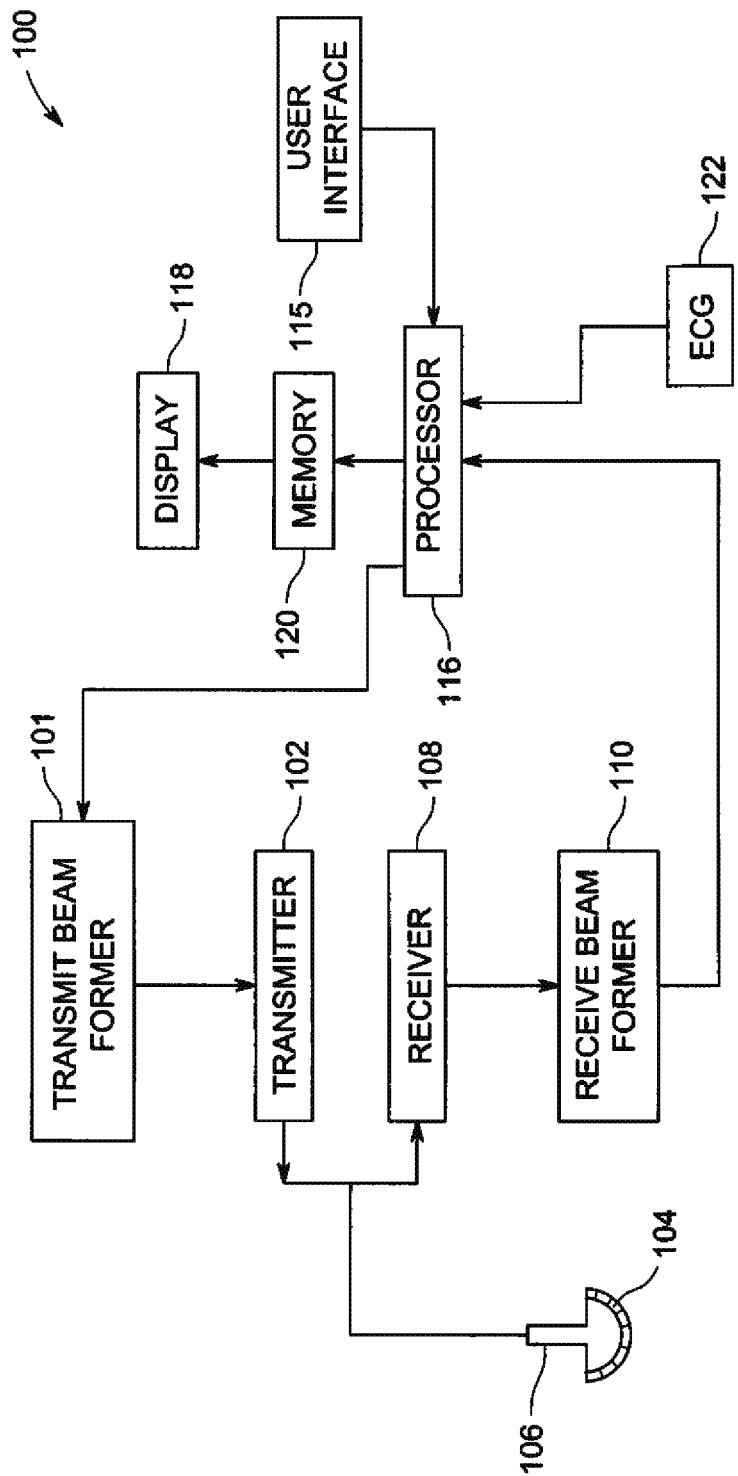
FIG. 1 is a schematic diagram of an ultrasound imaging system.

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

FIG. 1 is a schematic diagram of an ultrasound imaging system 100. The ultrasound imaging system 100 includes a transmit beamformer 101 and a transmitter 102 that drive transducer elements 104 within a probe 106 to emit pulsed ultrasonic signals into a body (not shown). A variety of geometries of probes and transducer elements may be used. The pulsed ultrasonic signals are back-scattered from structures in the body, like blood cells or muscular tissue, to produce echoes that return to the transducer elements 104. After the receiver 108, the electrical signals pass through a receive beamformer 110 that outputs ultrasound data. According to some embodiments, the probe 106 may contain electronic circuitry to do all or part of the transmit and/or the receive beam forming. For example, all or part of the transmit beamformer 101, the transmitter 102, the receiver 108 and the receive beamformer 110 may be situated within the probe 106. The terms "scan" or "scanning" may also be used in this disclosure to refer to acquiring data through the process of transmitting and receiving ultrasonic signals. A user interface 115 may be used to control operation of the ultrasound imaging system 100, including, to control the input of patient data, to change a scanning or display parameter, and the like.

The ultrasound imaging system 100 also includes a processor 116 in electronic communication with the probe 106. The processor 116 controls the transmit beamformer 101, the transmitter 102, the receiver 108 and the receive beamformer 110. By controlling the transmit beamformer 101 and the transmitter 102, the processor 116 controls the probe 106 to emit ultrasound beams in the desired shape and the processor 116 controls the probe 116 to steer the ultrasound beams in the desired direction. The processor 116 controls which of the transducer elements are active and the shape of a beam emitted from the probe 106. The processor is also in electronic communication with the display 118, and the processor 116 may process the ultrasound data into one or more image frames for display on the display 118. The processor 116 may comprise a central processor (CPU) according to an embodiment. According to other embodiments, the processor 116 may comprise other electronic components capable of carrying out processing functions, such as a digital signal processor, a field-programmable gate array (FPGA) or a graphic board. According to other embodiments, the processor 116 may comprise multiple electronic components capable of carrying out processing functions. For example, the processor 116 may comprise two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment the demodulation can be carried out earlier in the processing chain. The processor 116 is adapted to perform one or more processing operations according to a plurality of selectable ultrasound modalities on the data. The ultrasound data may be processed in real-time during a scanning session as the echo signals are received. A dynamic image may be displayed while ultrasound data is being acquired. For purposes of this disclosure, the term "dynamic image" is defined to include an image comprising a plurality of separate image frames displayed in sequence. For the purposes of this disclosure, the term "real-time" is defined to include a procedure that is performed without any intentional delay. For example, an embodiment may acquire and display a dynamic image with a real-time frame-rate of 7-20 frames/sec. It should be understood by those skilled in the art that the real-time frame rate may be dependent on the length of time that it takes to acquire each frame of ultrasound data for display. Accordingly, when acquiring a relatively large volume of data, the real-time frame rate may be slower. Thus, some embodiments may have real-time frame-rates that are considerably faster than 20 frames/sec while other embodiments may have real-time frame-rates slower than 7 frames/sec. The ultrasound information may be stored temporarily in a buffer (not shown) during a scanning session and processed in less than real-time in a live or off-line operation. Some embodiments of the invention may include multiple processors (not shown) to handle the processing tasks. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire ultrasound data at a frame-rate of, for example, 10 Hz to 30 Hz. Images generated from the data may be refreshed at a similar frame rate. Other embodiments may acquire and display ultrasound data at different rates. For example, some embodiments may acquire data at a frame rate of less than 10 Hz or water than 30 Hz depending on the size of the volume and the intended application. A memory 120 is included for storing processed frames of acquired data. In an exemplary embodiment, the memory 120 is of sufficient capacity to store at least several seconds worth of frames of ultrasound data. The frames of data are stored in a manner to facilitate retrieval thereof according to its order or time of acquisition. The memory 120 may comprise any known data storage medium. There is an ECG 122 attached to the processor 116 of the ultrasound imaging system 100 shown in FIG. 1. The ECG may be connected to the patient and provides cardiac data from the patient to the processor 116 for use during the acquisition of gated data.

Optionally, embodiments of the present invention may be implemented utilizing contrast agents. Contrast imaging generates enhanced images of anatomical structures and blood flow in a body when using ultrasound contrast agents including microbubbles. Separation of harmonic components from the received signals is performed using suitable filters. The use of contrast agents for ultrasound imaging is well-known by those skilled in the art and will therefore not be described in further detail.

In various embodiments of the present invention, ultrasound data may be processed by other or different mode-related modules within the processor 116 (e.g., B-mode, Color Doppler, M-mode, Color M-mode, spectral Doppler, TVI, strain, strain rate, and the like) to form 2D or 3D data. For example, one or more modules may generate B-mode, color Doppler, M-mode, color M-mode, spectral Doppler, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from coordinates beam space to display space coordinates. A video processor module may be provided that reads the image frames from a memory and displays the image frames in real time while a procedure is being carried out on a patient. A video processor module may store the image frames in the memory 120, from which the images are read and displayed.

Figure 2:
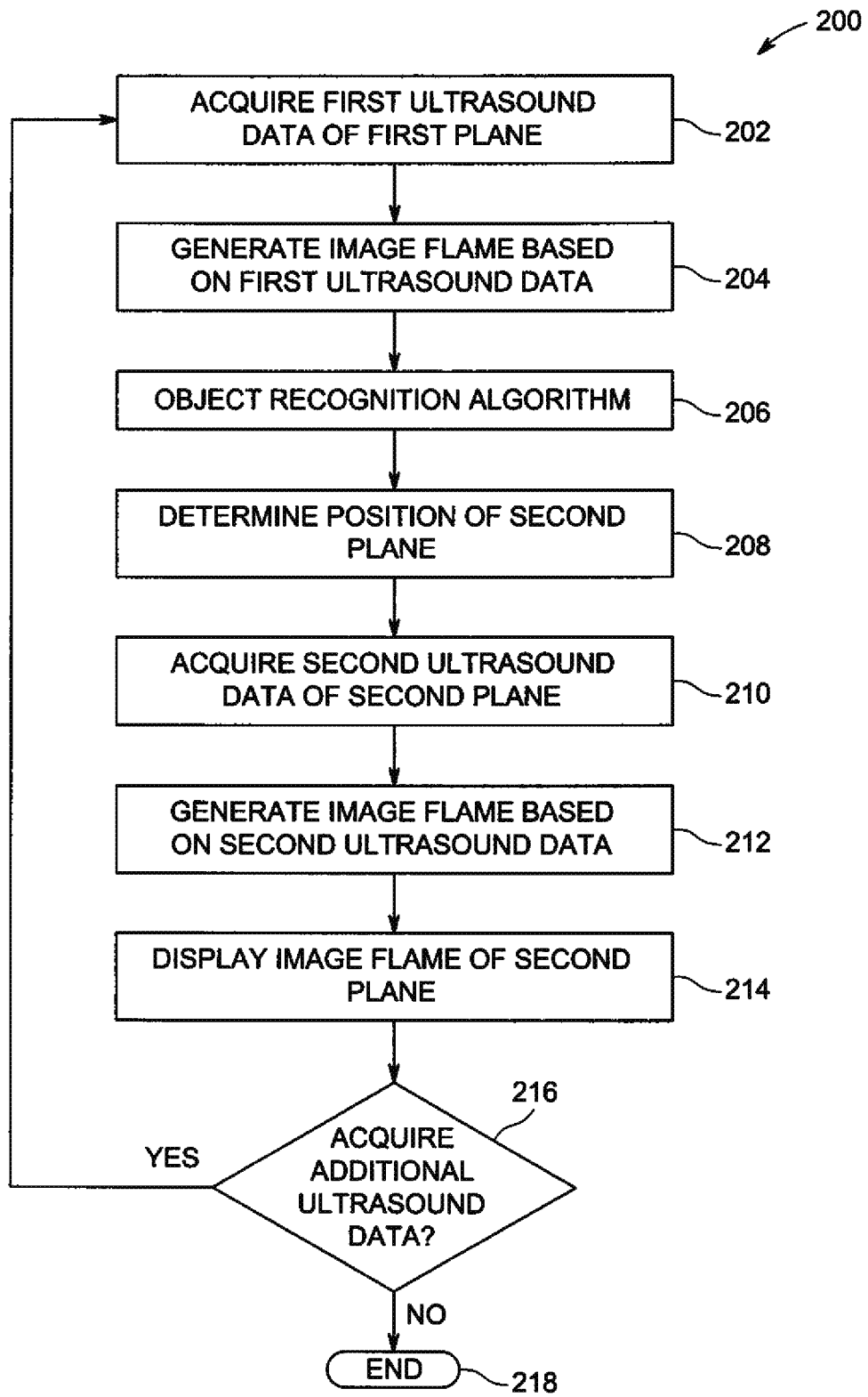
FIG. 2 is a flow chart of a method in accordance with an embodiment.

FIG. 2 is a flow chart of a method in accordance with an embodiment. The individual blocks represent steps that may be performed in accordance with the method 200. Additional embodiments may perform the steps shown in a different sequence and/or additional embodiments may include additional steps not shown in FIG. 2. The technical effect of the method 200 is the acquisition of anatomically correct ultrasound data of a plane. An additional technical effect is the display of a dynamic image with reduced artifacts caused by out-of-plane motion. The method 200 may be performed with an ultrasound imaging system such as the ultrasound imaging system 100 shown in FIG. 1.

Figure 3:
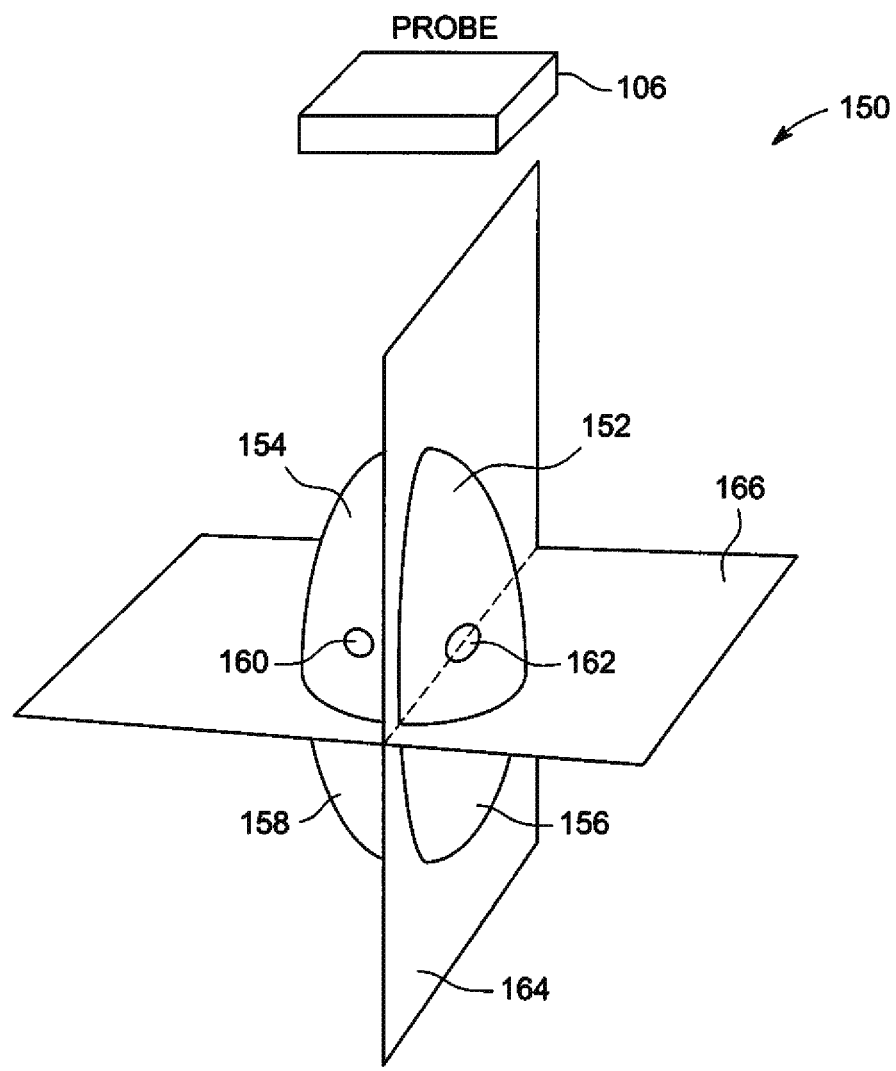
FIG. 3 is a schematic representation of a perspective view of a heart intersected by two planes in accordance with an embodiment.

FIG. 3 is a schematic representation of a perspective view of a heart intersected by two planes in accordance with an embodiment. The heart 150 comprises four chambers: a left atrium 152, a right atrium 154, a left ventricle 156 and a right ventricle 158. A right atrioventricular valve 160 separates the right ventricle 158 from the right atrium 154, and a left atrioventricular valve 162 separates the left atrium 152 from the left ventricle 156. Other interior structures of the heart 150, including walls of the chambers and major arteries are not shown in FIG. 3. A first plane 164 is shown intersecting the heart 150. The first plane 164 may comprise a parasternal long-axis plane in accordance with the embodiment of FIG. 3. A second plane 166 is shown as well. The second plane 166 intersects with the first plane 164 and may comprise an atrioventricular plane in accordance with the embodiment shown in FIG. 3. According to an embodiment, the second plane 166 may intersect one or both of the right atrioventricular valve 160 and the left atrioventricular valve 162. The probe 106 from the ultrasound imaging system 100 (shown in FIG. 1) is schematically represented with respect to the heart 150 and the two planes (164, 166) in accordance with an embodiment.

Referring now to FIG. 1, FIG. 2, and FIG. 3, at step 202 the processor 116 controls the probe 106 to acquire first ultrasound data of the first plane 164. The first ultrasound data of the first plane 164 may include either two-dimensional ultrasound data of the first plane or slab ultrasound data including the first plane. The term "two-dimensional ultrasound data" is well-known to those skilled-in-the-art and includes that acquisition of ultrasound data of a plane. For purposes of this disclosure, the term "slab ultrasound data" will be defined to include ultrasound data of a volume that is slab-shaped. That is, "slab ultrasound data" will include data for a volume that includes a plane with an additional thickness dimension when compared to "two-dimensional ultrasound data." At step 204, the processor 116 generates an image frame based on the ultrasound data of the first plane 164. At step 206, the processor 116 implements an object recognition algorithm on the image frame generated based on the first ultrasound data.

One example of an object recognition algorithm includes the method as described in U.S. patent application No. 2010/0195881, entitled "Method and Apparatus for Automatically Identifying Image Views in a 3D Dataset," assigned to the same Applicant and herein incorporated by reference in its entirety. For example, according to an exemplary embodiment, the method may comprise fitting a deformable model to one or more structures shown in an image frame. Then, based on the deformable model, the algorithm is able to identify feature points in the image frame. For example, the processor 116 may use a deformable model of a heart in order to identify one of the atrioventricular valves such as the left atrioventricular valve 162. Additional details about the object recognition algorithm will be discussed hereinafter. In a real-time scanning environment, additional image frames are acquired as long as an operator continues to scan the patient. According to an embodiment, the processor 116 may perform an object recognition algorithm on each image frame as additional ultrasound data is acquired. One advantage of using a deformable model as part of the object recognition algorithm is that it allows for the very rapid identification of a structure of interest within each image frame, which is particularly advantageous when displaying an image that updates in real-time. According to other embodiments, the processor 116 may use the object recognition algorithm to track the position of a landmark over a period of time.

The object recognition algorithm may be used to identify a landmark or a structure of interest based on the first ultrasound data. According to an embodiment, it may be desired to display an image of the patient's anatomy based on second ultrasound data of the second plane 166. The processor 116 may use the object recognition algorithm to identify one or more features that are indicative of a structure of interest or a landmark within the first plane 164. According to the embodiment of FIG. 3, the first plane 164 may include a parasternal long-axis plane through the left atrioventricular valve. The processor 116 may, for example, identify the position of an atrioventricular wall (not shown) or the position of one of the atrioventricular valves (160, 162) in the first ultrasound data of the first plane 164. Then, during step 208, based on the position of a landmark, such as the atrioventricular wall (not shown) in the first ultrasound data, the processor 116 may then determine a position for the second plane 166 relative to the probe 106. It should be appreciated that other embodiments may use different landmarks and/or structures of interest in the first ultrasound data in order to determine the position the second plane 166 with respect to the probe 106. Additionally, according to other embodiments, the landmark may comprise a feature or a portion of the structure of interest.

Still referring to FIGS. 1, 2 and 3, at step 210, the processor 116 controls the probe 106 to acquire second ultrasound data of the second plane 166 at the position that was determined during step 210. At step 212, the processor 116 generates an image frame based on the second ultrasound data of the second plane 166 acquired during step 210. According to an exemplary embodiment, the image frame may be a gray scale image. However, in other embodiments, the image frame generated at step 212 may include an image generated according to another ultrasound modality, such as: Color Doppler, spectral Doppler, TVI, strain, strain rate, and the like.

At step 214, the processor 116 displays the image frame generated at step 212 on the display device 118. At step 216, the processor 116 determines if an additional ultrasound data should be acquired. According to an embodiment, the method 200 may continue acquiring additional ultrasound data at step 216 until an operator terminates the ultrasound examination. If the acquisition of additional ultrasound data is desired at step 216, the method 200 returns to step 202, where the steps 202, 204, 206 208, 210, 212, 214, and 216 are repeated an additional time. According to an embodiment, the first plane 164 is defined with respect to the probe 106. Meanwhile, the position of the second plane 166 may be adjusted in real-time in order to track the motion of a landmark as detected in the first plane. For example, according to an embodiment described previously, the position of the second plane 166 is adjusted to track the motion of an atrioventricular wall as detected based on first ultrasound data of the first plane 164. For example, if it is desired to acquire ultrasound data of the left atrioventricular valve 162, the position of the second plane 166 may be adjusted during each iteration of steps 202, 204, 206 208, 210, 212, 214, and 216 so that the positioning of the second plane 166 compensates for movement of the left atrioventricular valve 162 detected based on ultrasound data of the first plane 164. The position of the second plane may be adjusted during each iteration of steps 202, 204, 206 208, 210, 212, 214, and 216 so that the second plane 166 maintains a generally constant orientation with respect to the landmark that is being tracked in the first plane 164. According to an embodiment, the processor 116 may adjust the position of the second plane by translating the position of the second plane in a direction contained within the first plane. In other words, the second plane may keep a fixed orientation with respect to the probe 106, while being translated in position with respect to the probe 106. According to other embodiments, the second plane may be adjusted through a combination of translation and tilting.

According to an exemplary embodiment, the method 200 may cycle through many iterations of steps 202, 204, 206 208, 210, 212, 214, and 216. Multiple iterations of steps 202, 204, 206 208, 210, 212, 214, and 216 will result in the acquisition of additional first ultrasound data of the first plane 164 and additional second ultrasound data of the second plane 166. The image frame displayed at step 214 during each subsequent iteration of steps 202, 204, 206 208, 210, 212, 214, and 216 may replace the image frame from the previous iteration. The multiple iterations of steps 202, 204, 206 208, 210, 212, 214, and 216 may result in the display of a dynamic image of the second plane 166. According to an exemplary embodiment, the image frame of the second plane 166 (shown in FIG. 3) displayed at step 214 may be updated in real-time as the processor 116 controls the acquisition of additional second ultrasound data at step 210 during multiple iterations of steps 202, 204, 206 208, 210, 212, 214, and 216.

Each iteration through steps 202, 204, 206 208, 210, 212, 214, and 216, the method 200 acquires additional first ultrasound data of the first plane 164 at step 202 and generates a new image frame of the first plane at step 204. As described hereinabove, the method 200 applies an object recognition algorithm in order to locate a landmark in the image frame of the first plane 164. According to the exemplary embodiment, the processor 116 may use the landmark to determine the location of the atrioventricular plane. By performing the object recognition algorithm on each newly acquired image frame of the first plane 164, it is possible for the processor 116 to adjust the position of the second plane 166 with each iteration of steps 202, 204, 206 208, 210, 212, 214, and 216 in order to more precisely capture the structure of interest, which, according to an embodiment, may include the either the right atrioventricular valve 160 or the left atrioventricular valve 162. The method 200 allows the processor to display a dynamic image of the second plane 166 with fewer artifacts caused by out-of plane movement. In other words, by tracking the motion of a landmark based on ultrasound data of the first plane, the processor 116 is able to adjust the position of the second plane 166, and hence the location of the ultrasound data acquired by the probe 106, in order compensate for the motion detected in the first plane 164. And, if at step 216, no additional ultrasound data are required, then the method 200 proceeds to step 218 where the method ends.

Figure 4:
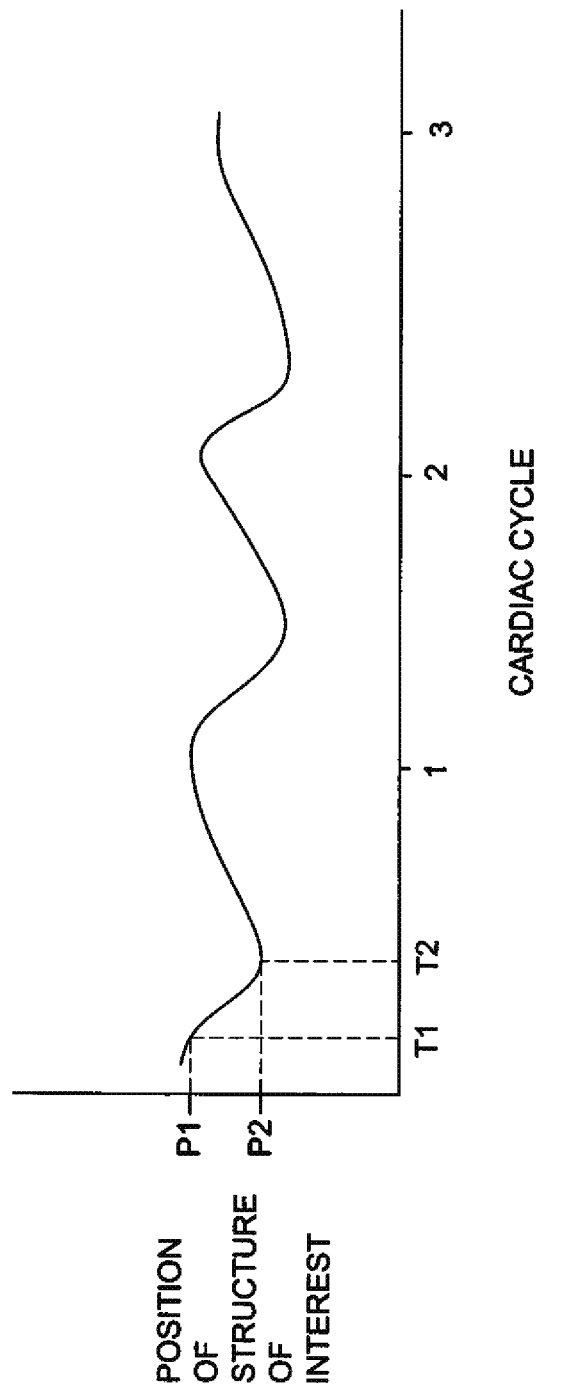
FIG. 4 is a chart showing an example of position versus time for a structure of interest in accordance with an embodiment.

Referring to FIG. 4, a chart showing an example of position vs. time for structure of interest is shown. As discussed previously, the structure of interest may include an atrioventricular valve according to an embodiment. The chart in FIG. 4 shows that the structure of interest moves in a periodic fashion within a first plane during each cardiac cycle. Since it may be desired to generate a dynamic image of a plane passing through a specific anatomical structure, the method 200 shown in FIG. 3 allows the processor 116 (shown in FIG. 1) to track the motion of the structure of interest in a first plane and to acquire motion-corrected ultrasound data of a structure of interest as the structure of interest moves with respect to the probe 106. The processor 116 may be further adapted display a dynamic image of the structure of interest based on the motion-corrected ultrasound data. For example, at a time T1, the structure of interest is at a position P1. Then, at a time T2, the structure of interest is at a position P2. In order to acquire a first ultrasound data of a plane through the structure of interest at time T1, it is necessary for the plane to pass through position P1. Likewise, in order to acquire a second ultrasound data of the plane through the structure of interest at the time T2, it is necessary for the plane to pass through position P2. As such, is would be necessary for the processor 116 (shown in FIG. 1) to control the acquisition so that the position of the plane is different with respect to an ultrasound probe at time T1 than at time T2. It should be appreciated that T1 and T2 are just two exemplary sample times and that it maybe desired to determine the position of the structure of interest at many additional points in time.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method of ultrasound imaging comprising:
using an ultrasound probe to acquire first ultrasound data, the first ultrasound data comprising data of a first plane through a structure of interest;
identifying, within the first ultrasound data, one or more features that are indicative of the structure of interest or a landmark within the first plane;
based on a location of the one or more features or the landmark within the first plane, determining a position, relative to the ultrasound probe, for a second plane;
using the ultrasound probe to acquire second ultrasound data, the second ultrasound data comprising data of the second plane through the structure of interest, the second plane being distinct from the first plane;
generating an image containing the structure of interest based on the second ultrasound data; and
displaying the image.

2. The method of claim 1, further comprising:
tracking movement of the structure of interest by:
using the ultrasound probe to acquire additional first ultrasound data, the additional first ultrasound data comprising data of a new first plane through the structure of interest, wherein the structure of interest within the new first plane has moved in relation to a location of the structure of interest within the first plane;
identifying, within the additional first ultrasound data, the one or more features that are indicative of the structure of interest or the landmark within the new first plane;
based on a location of the one or more features or the landmark within the new first plane, determining a new position, relative to the ultrasound probe, for a new second plane;
using the ultrasound probe to acquire additional second ultrasound data, the additional second ultrasound data comprising data of the new second plane through the structure of interest, the new second plane being distinct from the new first plane, wherein the new position of the new second plane is adjusted to compensate for the movement of the location of the structure of interest between the acquisition of the first plane and the new first plane;
generating a new image containing the structure of interest based on the additional second ultrasound data; and
displaying the new image.

3. The method of claim 2, wherein the image and the new image are displayed in sequence to comprise a dynamic image.

4. The method of claim 1, wherein said acquiring the second ultrasound data occurs during the process of acquiring the first ultrasound data.

5. The method of claim 4, wherein said acquiring the second ultrasound data is interleaved with said acquiring the first ultrasound data.

6. The method of claim 1, wherein the new position of the new second plane is adjusted in real-time while said tracking the movement of the structure of interest.

7. The method of claim 1, wherein the second ultrasound data comprises two-dimensional ultrasound data.

8. The method of claim 1, wherein the second ultrasound data comprises slab ultrasound data.

9. The method of claim 1, wherein the landmark comprises a portion of the structure of interest.

10. The method of claim 2, wherein the new position of the new second plane is adjusted to maintain a constant orientation with respect to the structure of interest within the second plane.

11. The method of claim 1, further comprising implementing an object recognition algorithm with a processor to identify the one or more features or the landmark in the first ultrasound data.

12. The method of claim 11, wherein the object recognition algorithm comprises fitting a deformable model to the first ultrasound data to identify the one or more features or the landmark in the first ultrasound data.

13. The method of claim 1, wherein the position of the second plane is adjusted by translating the position of the second plane with respect to the probe.

14. The method of claim 1, wherein the second plane is disposed at an angle with respect to the first plane.

15. An ultrasound imaging system comprising:
a probe configured to acquire ultrasound data;
a display device; and
a processor in electronic communication with both the probe and the display device, wherein the processor is configured to:
control the probe to acquire first ultrasound data, the first ultrasound data comprising data of a first plane through a structure of interest;
identify, within the first ultrasound data, one or more features that are indicative of the structure of interest or a landmark within the first plane;
based on the location of the one or more features or the landmark within the first plane, determine a position, relative to the ultrasound probe, for a second plane;
control the probe to acquire second ultrasound data, the second ultrasound data comprising data of the second plane through the structure of interest, the second plane being distinct from the first plane;
generate an image based on the second ultrasound data; and
display the image on the display device.

16. The ultrasound imaging system of claim 15, wherein the processor is further configured to control the probe to acquire the second ultrasound data during the process of acquiring the first ultrasound data.

17. The ultrasound imaging system of claim 15, wherein the second ultrasound data comprises slab ultrasound data.

18. The ultrasound imaging system of claim 15, wherein the first ultrasound data comprises slab ultrasound data.

19. The ultrasound imaging system of claim 15, wherein the processor is further configured to control the probe to interleave the acquisition of the second ultrasound data with the acquisition of the first ultrasound data.

20. The ultrasound imaging system of claim 15, wherein the processor is further configured to implement an object recognition algorithm to identify the one or more features or the landmark in the first ultrasound data.

21. The ultrasound imaging system of claim 20, wherein the processor is further configured to fit a deformable model to the first ultrasound data to identify the one or more features or the landmark in the first ultrasound data.

22. The ultrasound imaging system of claim 15, wherein the processor is further configured to:
control the probe to acquire additional first ultrasound data, the additional first ultrasound data comprising data of a new first plane through the structure of interest, wherein the structure of interest within the new first plane has moved in relation to a location of the structure of interest within the first plane;
identify, within the additional first ultrasound data, the one or more features that are indicative of the structure of interest or the landmark within the new first plane;
based on a location of the one or more features or the landmark within the new first plane, determine a new position, relative to the probe, for a new second plane;
control the probe to acquire additional second ultrasound data, the second ultrasound data comprising data of the new second plane through the structure of interest, the new second plane being distinct from the new first plane, wherein the new position of the new second plane is adjusted to compensate for the movement of the location of the structure of interest between the first plane and the new first plane;

generate a new image containing the structure of interest based on the additional second ultrasound data; and display the new image on the display device, wherein the image and the new image are displayed in sequence to comprise a dynamic image.

* * * * *